(12) United States Patent
Evans, V et al.

(10) Patent No.: US 9,965,869 B1
(45) Date of Patent: May 8, 2018

(54) SENSING LIGHT THROUGH A SURFACE WITH A RESIDUE

(71) Applicant: Essential Products, Inc., Palo Alto, CA (US)

(72) Inventors: David John Evans, V, Palo Alto, CA (US); Xinrui Jiang, San Jose, CA (US); Andrew E. Rubin, Los Altos, CA (US); Matthew Hershenson, Los Altos, CA (US); Xiaoyu Miao, Palo Alto, CA (US); Joseph Anthony Tate, San Jose, CA (US); Jason Sean Gagne-Keats, Cupertino, CA (US)

(73) Assignee: ESSENTIAL PRODUCTS, INC., Palo Alto, CA (US)

( * ) Notice: Subject to any disclaimer, the term of this patent is extended or adjusted under 35 U.S.C. 154(b) by 0 days. days.

(21) Appl. No.: 15/655,155

(22) Filed: Jul. 20, 2017

Related U.S. Application Data

(60) Provisional application No. 62/514,582, filed on Jun. 2, 2017.

(51) Int. Cl.
    *G06T 7/62*     (2017.01)
    *G06N 99/00*     (2010.01)
    *G01N 21/01*     (2006.01)

(52) U.S. Cl.
    CPC ............... *G06T 7/62* (2017.01); *G01N 21/01* (2013.01); *G06N 99/005* (2013.01); *G01N 2021/0137* (2013.01)

(58) Field of Classification Search
    CPC ............ H04N 1/4097; H04N 1/00307; H04N 5/2171; G06K 9/346; G06T 5/005; G06T 2207/10016
See application file for complete search history.

(56) References Cited

U.S. PATENT DOCUMENTS

| | | | | |
|---|---|---|---|---|
| 2003/0090742 A1* | 5/2003 | Fukuda | ............... | H04N 1/04 358/448 |
| 2010/0321537 A1* | 12/2010 | Zamfir | ............... | H04N 5/217 348/241 |
| 2017/0038459 A1* | 2/2017 | Kubacki | ............... | G01S 17/36 |

OTHER PUBLICATIONS

"Removing Image Artifacts Due to Dirty Camera Lenses and Thin Occluders"; retrieved online from url: http://www1.cs.columbia.edu/CAVE/projects/dirtylens/; Columbia Vision and Graphics Center, Dept. of Computer Science, Columbia University; 3 pages.

(Continued)

*Primary Examiner* — Edward Park
(74) *Attorney, Agent, or Firm* — Perkins Coie LLP

(57) ABSTRACT

In one embodiment, a light sensor, such as a camera, records an image through the surface with the residue to produce a stained image. A processor associated with the camera identifies object outlines within the image using a machine learning model, and smooth the colors within the object outlines. In another embodiment, the light sensor is placed beneath a dual-mode region of a display containing the residue. The dual-mode region can be opaque and function as part of the display, or can be transparent and allow environment light to reach the light sensor. Initially, the processor determines the position of the residue by causing the dual-mode region to display a predetermined pattern, while the light sensor records the predetermined pattern. Using the determined position of the residue, the processor corrects the pixels within the residue in the recorded image, by interpolating the values of the pixels outside of the residue.

11 Claims, 15 Drawing Sheets

(56) References Cited

OTHER PUBLICATIONS

Gu, Jinwei et al.; "Removing Image Artifacts Due to Dirty Camera Lenses and Thin Occluders"; retrieved online from url: https://cseweb.ucsd.edu/~ravir/dirtylens.pdf; ACM Transactions on Graphics (Proceedings of SIGGRAPH Asia), Dec. 2009;10 pages.

\* cited by examiner

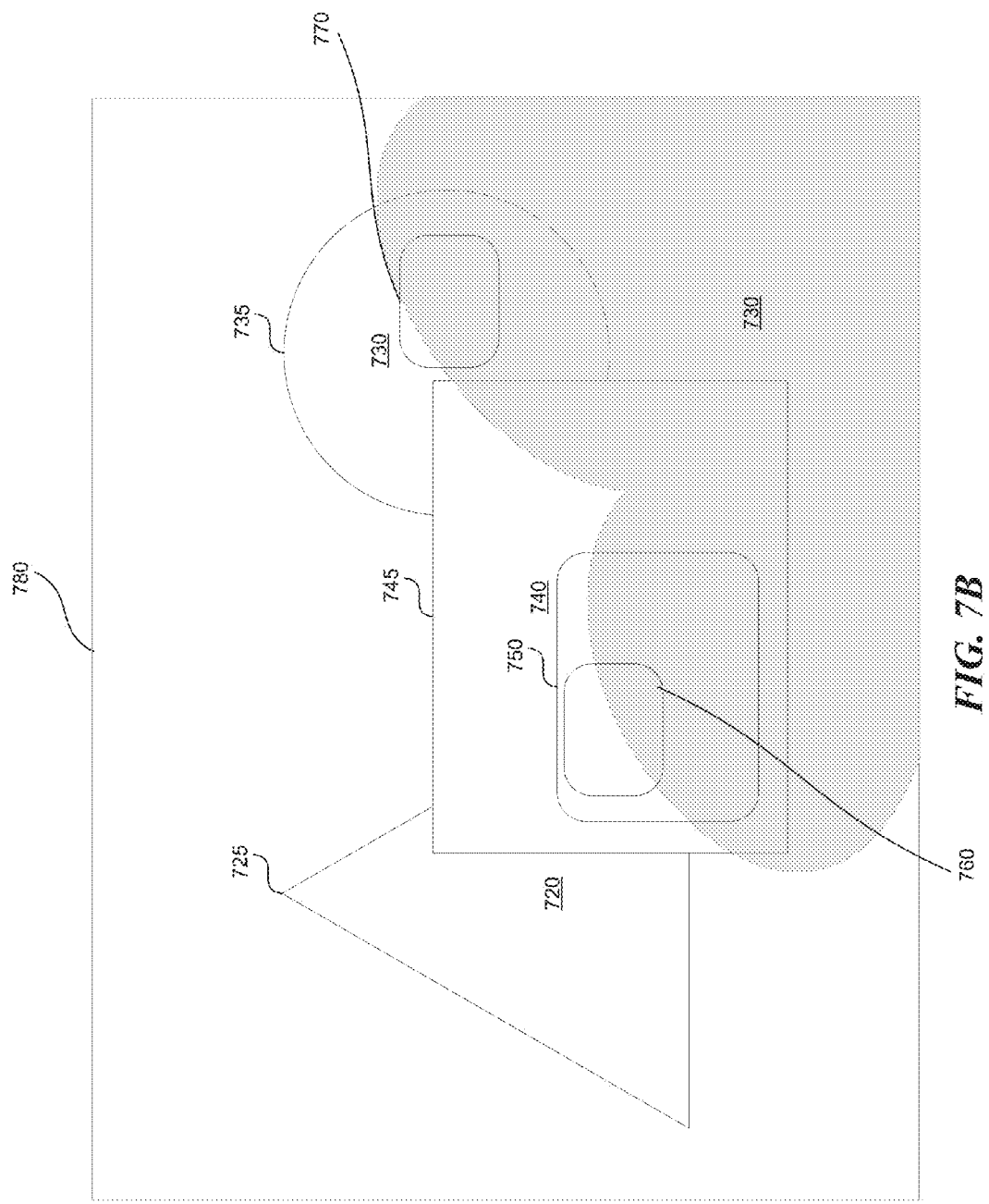

SENSING LIGHT THROUGH A SURFACE WITH A RESIDUE

CROSS-REFERENCE TO RELATED APPLICATIONS

This application claims priority to the U.S. provisional patent application Ser. No. 62/514,582 filed Jun. 2, 2017.

TECHNICAL FIELD

The present application is related to light sensing, and more specifically to methods and systems that sense light through a surface with a residue.

BACKGROUND

Touchscreen mobile devices with light sensors are in wide use today. By touching the screen a user leaves fingerprints on the screen, sometimes in the area where the light sensor is located. Consequently, the light sensor needs to sense light through a stained surface, i.e., surface with a residue.

SUMMARY

Presented here are system and methods for sensing light through a surface with a residue. In one embodiment, a light sensor, such as a camera, records an image through the surface with the residue to produce a stained image. A processor associated with the camera identifies object outlines within the image using a machine learning model, and smooth the colors within the object outlines. In another embodiment, the light sensor is placed beneath a dual-mode region of a display containing the residue. The dual-mode region can be opaque and function as part of the display, or can be transparent and allow environment light to reach the light sensor. Initially, the processor determines the position of the residue by causing the dual-mode region to display a predetermined pattern, while the light sensor records the predetermined pattern. Using the determined position of the residue, the processor corrects the pixels within the residue in the recorded image, by interpolating the values of the pixels outside of the residue.

BRIEF DESCRIPTION OF THE DRAWINGS

FIG. 7B shows an image of environment recorded by the light sensor through the residue, according to another embodiment.

DETAILED DESCRIPTION

Light Sensor

Presented here are system and methods for sensing light through a surface with a residue. In one embodiment, a light sensor, such as a camera, records an image through the surface with the residue to produce a stained image. A processor associated with the camera identifies object outlines within the image using a machine learning model, and smooth the colors within the object outlines. In another embodiment, the light sensor is placed beneath a dual-mode region of a display containing the residue. The dual-mode region can be opaque and function as part of the display, or can be transparent and allow environment light to reach the light sensor. Initially, the processor determines the position of the residue by causing the dual-mode region to display a predetermined pattern, while the light sensor records the predetermined pattern. Using the determined position of the residue, the processor corrects the pixels within the residue in the recorded image, by interpolating the values of the pixels outside of the residue.

Figure 1A:
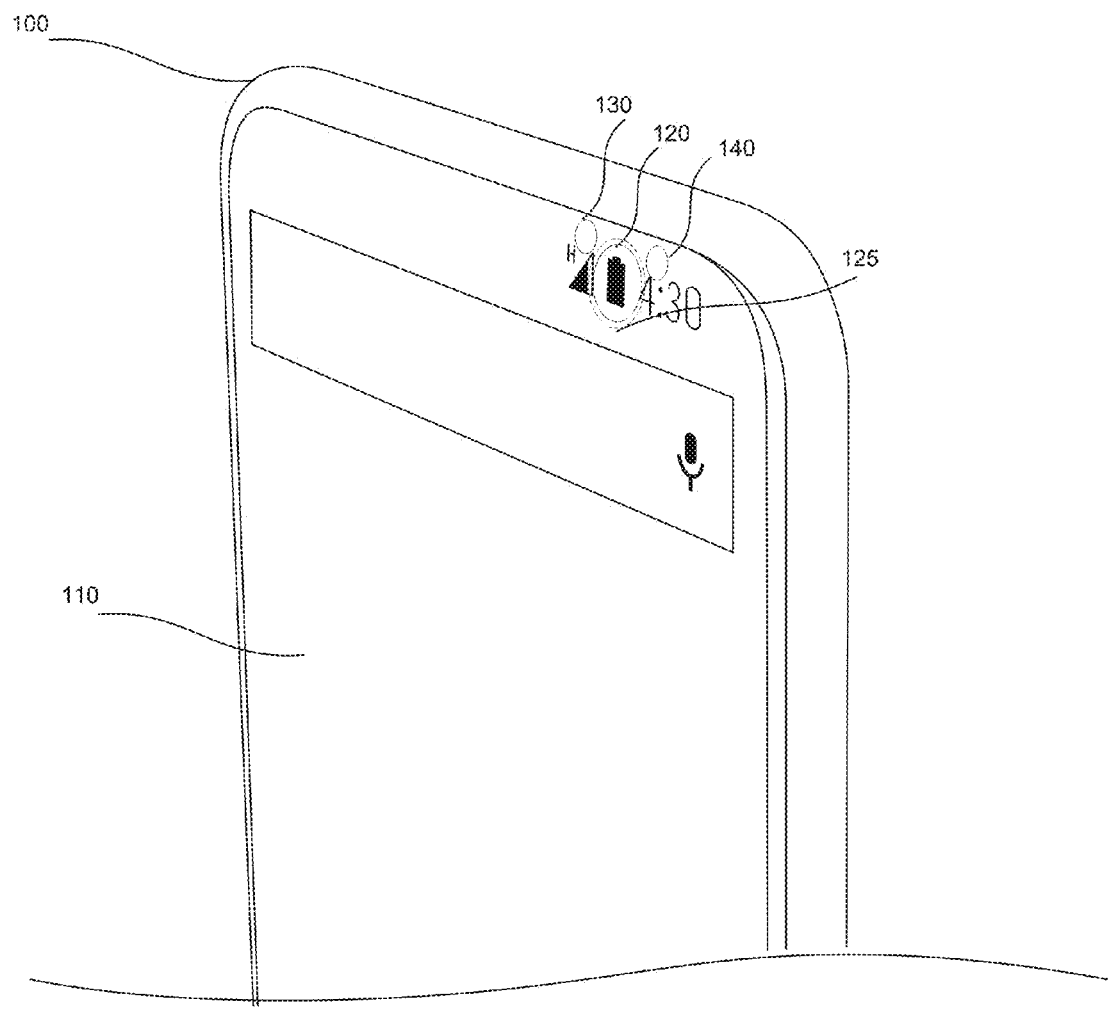
FIG. 1A shows a light sensor beneath a display.

FIG. 1A shows a light sensor beneath a display. A mobile device 100 includes the display 110, a light sensor 120, optional additional light sensors 130, 140, and a display controller (not pictured), such as a processor, to control a region 125 of the display 110. In one embodiment the region 125 can be a dual-mode region, while in another embodiment the region 125 can be permanently transparent, and not configured to act as a part of the display 110. When the region 125 is a dual-mode region, the dual-mode region 125 can be selectively addressable region as described in the U.S. patent application Ser. No. 15/336,380, filed March October 27, 2016, and incorporated by reference herein in its entirety. The display 110 can be a liquid crystal display (LCD), an organic light emitting diode (OLED) display, etc.

The region 125 can be the same size as the light sensor 120, can be smaller than the light sensor 120, or can be larger than the light sensor 120. The region 125 is placed above the light sensor 120. When the region 125 is dual-mode, the dual-mode region 125 can operate in a transparent mode and an opaque mode. Further, the whole display 110 can operate in a transparent mode and in an opaque mode. The dual-mode region 125 can become transparent or opaque at the same time as the rest of the display, or the dual-mode region 125 can become transparent or opaque independently of the rest of the display. When the dual-mode region 125 is in the transparent mode, the dual-mode region allows light to enter and exit through the dual-mode region 125. For example, when the light sensor 120 is a proximity sensor, the dual-mode region 125 turns transparent, and allows a beam of light, e.g., an infrared beam of light, from the proximity sensor to exit through the dual-mode region 125, and enter through the dual-mode region 125 back to the proximity sensor.

The display 110 becomes opaque when displaying opaque portions of a display image. The display 110 becomes substantially transparent when not displaying the display image. When the display 110 is displaying transparent portions of the image, the display 110 can be substantially transparent, the display 110 can be opaque, or, the display 110 can assume a degree of transparency corresponding to the degree of transparency of the display image. The display 110 can be optically transparent to the visible light, infrared light, etc.

The light sensor 120 is placed beneath the region 125 of the display 110. The light sensor 120 can be a camera, an ambient sensor, a proximity sensor, etc. The light sensor 120, and the optional additional light sensors 130, 140 can activate and deactivate. When the light sensor 120, and the optional additional light sensors 130, 140 activate, they can detect a property of incoming light, such as frequency, intensity, and/or time of flight of incoming light. For example, when the light sensor 120 is a camera, when the camera is active, the camera records an image, i.e. the camera detects frequency and intensity of incoming light. When the light sensor 120 is an ambient sensor, when the ambient sensor is active, the ambient sensor measures the intensity of ambient light. When the light sensor 120 is a proximity sensor, the proximity sensor emits a light beam, such as an infrared light beam, and measures a time of flight of the emitted light beam. From the time of flight of the emitted light beam, the proximity sensor determines distance to an object.

Figure 1B:
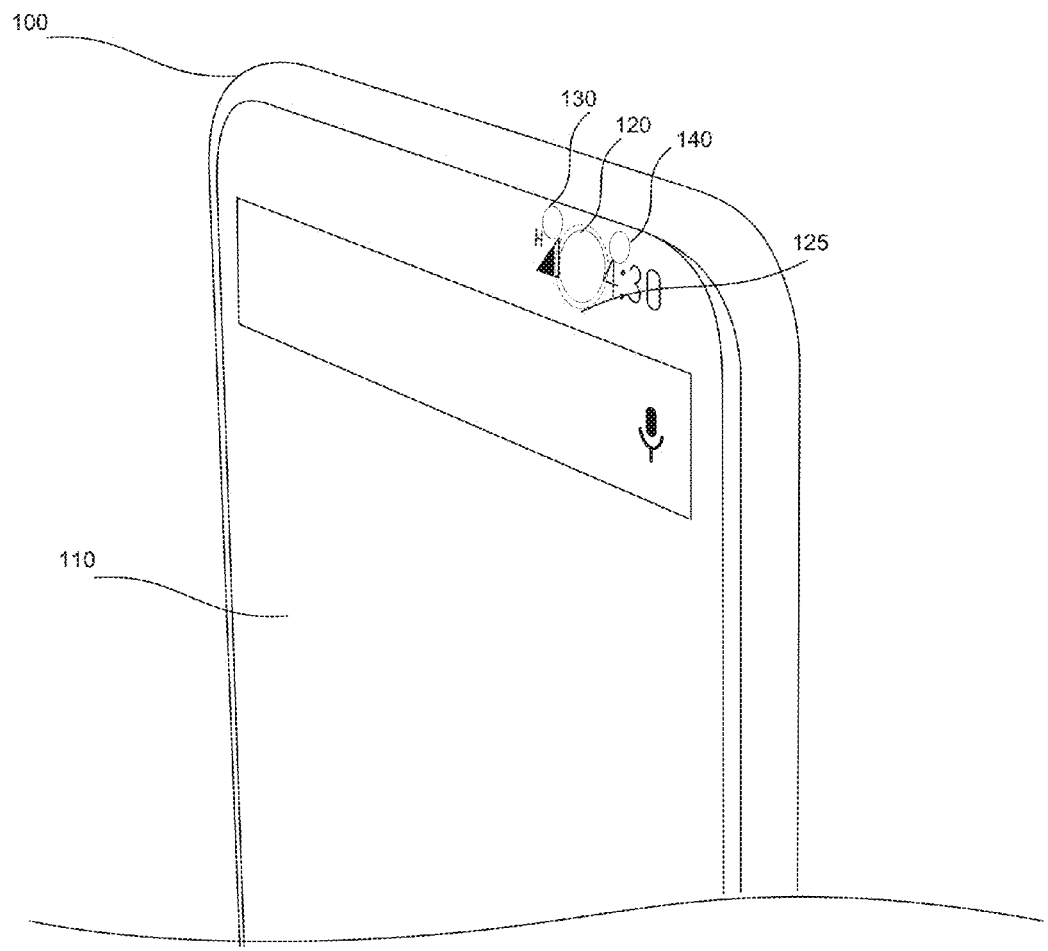
FIG. 1B shows a deactivated dual-mode region.

FIG. 1B shows a deactivated dual-mode region. When the light sensor 120, and/or optional additional light sensors 130, 140 activate, the display controller deactivates the dual-mode region corresponding to the light sensor 120, and/or the optional additional light sensors 130, 140. The display controller can deactivate the dual-mode region by sending a first signal to the dual-mode region to deactivate, and thus become transparent. Similarly, the display controller can activate the dual-mode region by sending a second signal to the dual-mode region to activate. In FIG. 1B, the light sensor 120 is active, and consequently the dual-mode region 125 of the display 110 stops displaying the display image, specifically, the battery icon.

As seen in FIG. 1B, the battery icon disappears from the display 110. When the dual-mode region 125 of the display 110 is inactive, the dual-mode region 125 becomes substantially transparent to enable the light sensor 120 to receive incoming light. In one embodiment, the size of the light sensor 120 is sufficiently small, so that the missing dual-mode region 125 of the display 110 tends to be unnoticeable to a user. Additionally or alternatively, the display controller can deactivate the dual-mode region 125 for a sufficiently short amount of time, so that the user does not have time to perceive the missing dual-mode region 125. For example, the sufficiently short amount of time can be less than 1/30 of a second.

Figure 1C:
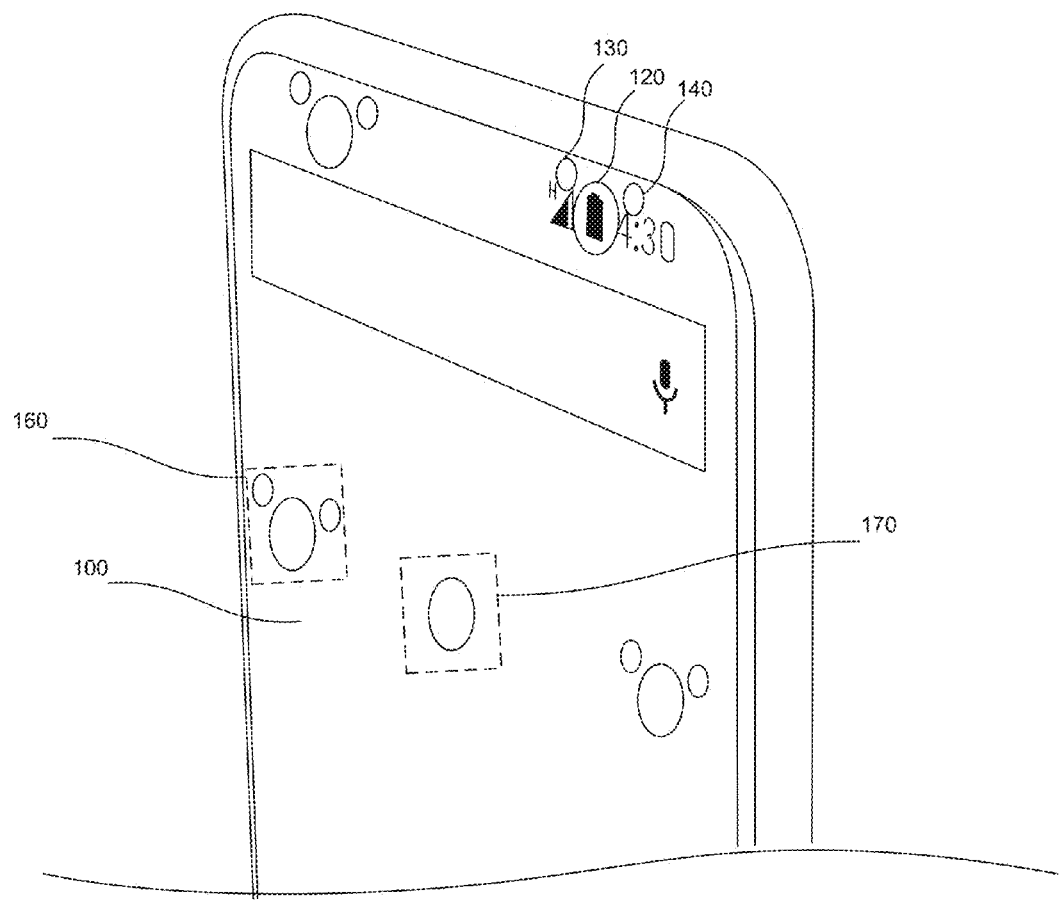
FIG. 1C shows a varying placement of the light sensors.

FIG. 1C shows a varying placement of the light sensors 120, 130, 140. The light sensors 120, 130, 140 can be placed proximate to each other, as seen in placement 160, or can be placed individually, as seen in placement 170. The light sensors 120, 130, 140 can take on various shapes such as a circle, an ellipse, a rectangle, a rectangle with at least one rounded edge, etc. The light sensors 120, 130, 140 can be placed anywhere on the screen, such as in corners of the screen, along the sides of the screen, in the center, etc.

Figure 2A:
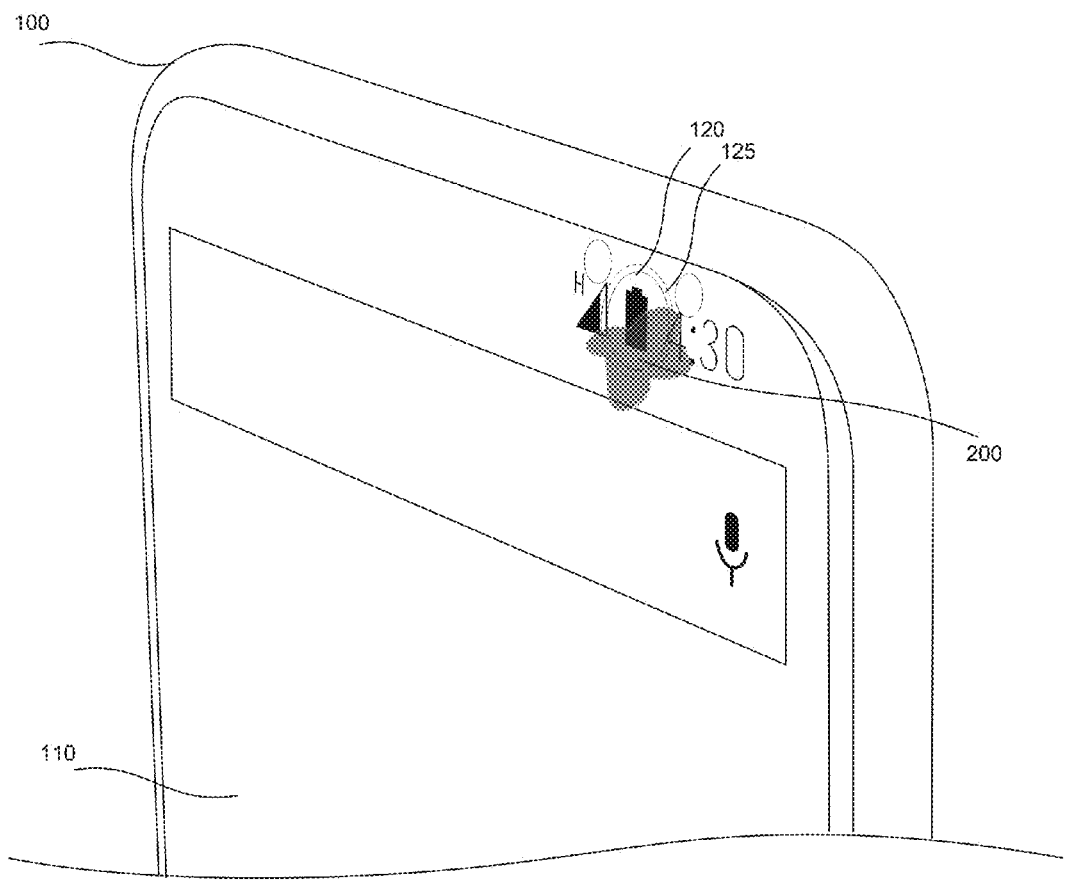
FIG. 2A shows a region with a residue.

FIG. 2A shows a region with a residue. The region 125 can be covered with a residue 200 such as dirt, dust, and/or oil from finger tips. For example, the light sensor 120 placed beneath the region 125 can be activated by touching the dual-mode region 125, as described in the patent application Ser. No. 15/165,887, filed May 26, 2016, and incorporated by reference herein in its entirety. By touching the region 125 residue 200 such as oil from fingertips can accumulate on the dual-mode region 125. Residue 200 can interfere with light from the environment reaching the light sensor 120. Described below are various methods to minimize and/or to remove the effect of the residue 200 on light reaching the light sensor 120.

Figure 2B:
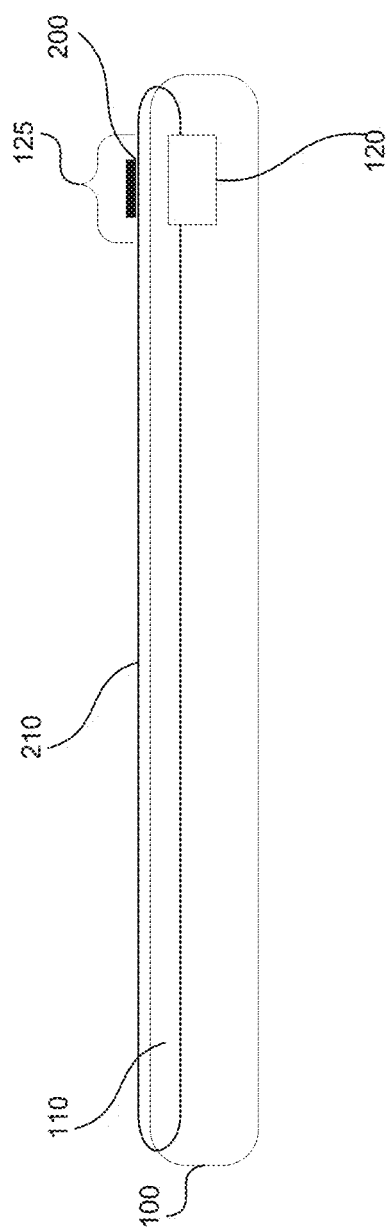
FIG. 2B shows a side view of a region covered with an oleophobic layer.

FIG. 2B shows a side view of a region 125 covered with an oleophobic layer. In one embodiment, to minimize the residue 200 in FIG. 2A accumulated on the region 125, an oleophobic layer 210 can be applied to the dual-mode region 125. The oleophobic layer 210 can be applied only to the dual-mode region 125, or can be applied to the whole display 110 of the mobile device 100. The oleophobic layer lacks an affinity to oils, thus minimizing the oil deposited on the oleophobic layer, and consequently on the dual-mode region 125.

Figure 3:
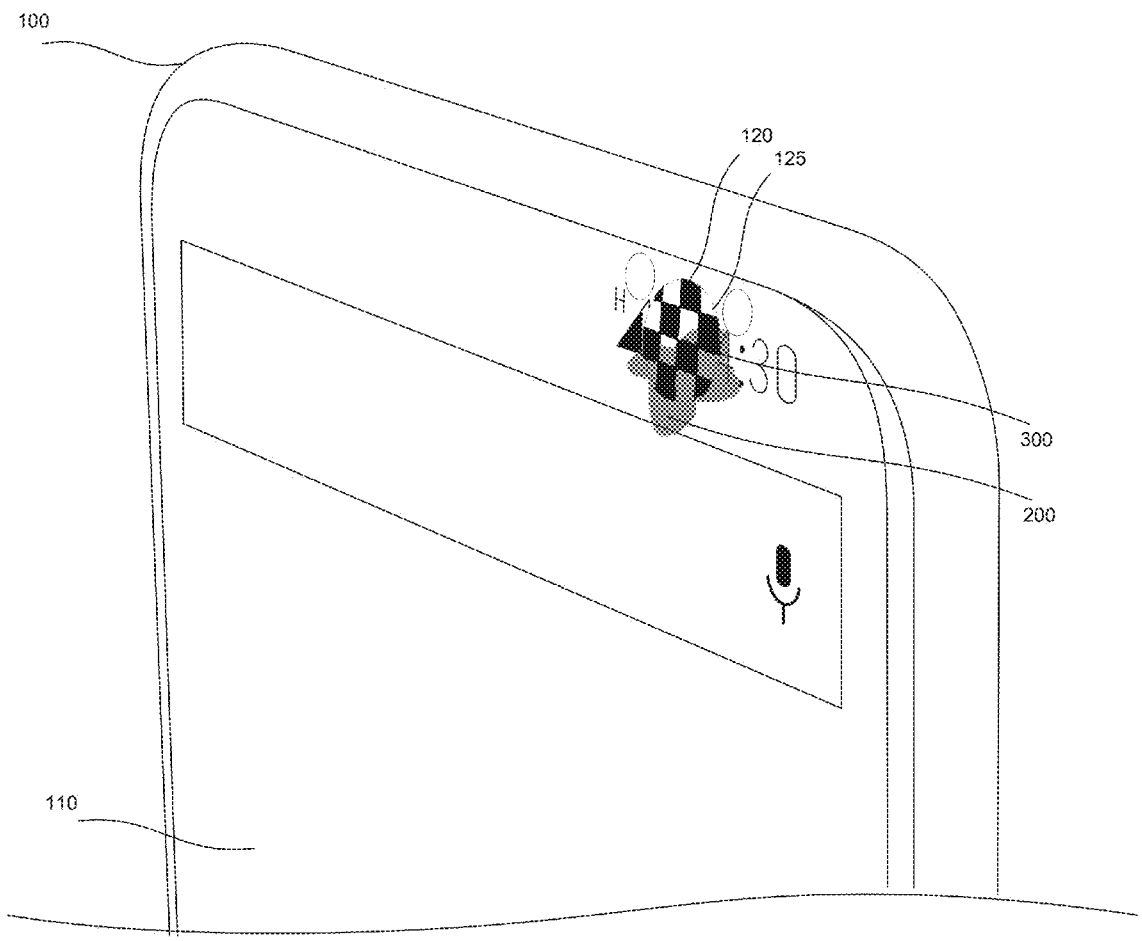
FIG. 3 shows a predetermined pattern displayed on a dual-mode region.

FIG. 3 shows a predetermined pattern displayed on a dual-mode region. To remove the effect of the residue 200 on the light sensor 120, the dual-mode region 125 can display a predetermined pattern 300, the light sensor 120 can detect light while the predetermined pattern 300 is being displayed, and based on the predetermined pattern and the detected light a processor can determine position of the residue 200.

The predetermined pattern 300 can be a checkerboard pattern as shown in FIG. 3, and can also be a grid, can consist of a combination of geometric shapes, can be colored, etc. Even though the residue 200 is located above the dual-mode region 125 and the light sensor 120, some light from the dual-mode region 125 bounces off the residue 200 and reaches the light sensor 120. Light emitted by the dual-mode region 125 bounces off the residue and reaches the light sensor 120, thus causing the image recorded by the light sensor 120 to be brighter in regions corresponding to the residue.

Figure 4B:
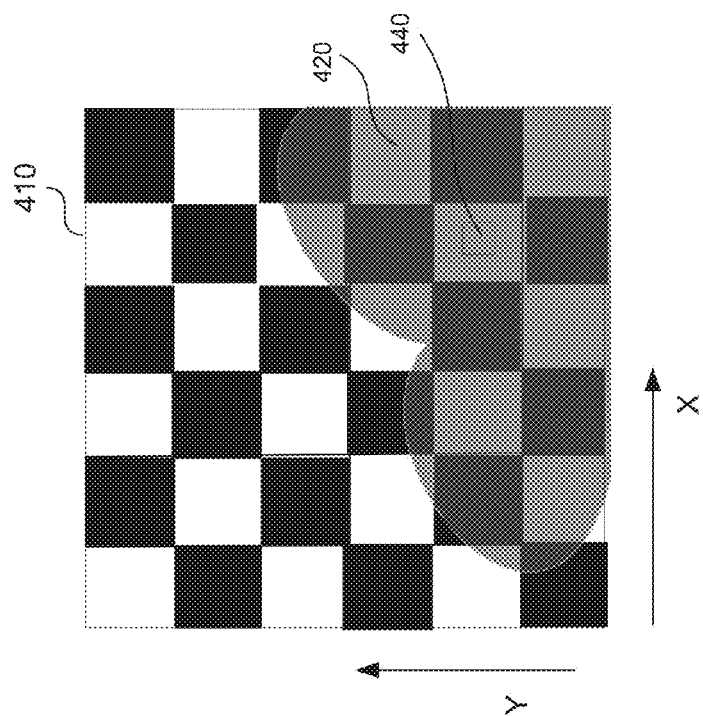
FIG. 4B shows the image of the predetermined pattern that is recorded by the light sensor.
Figure 4A:
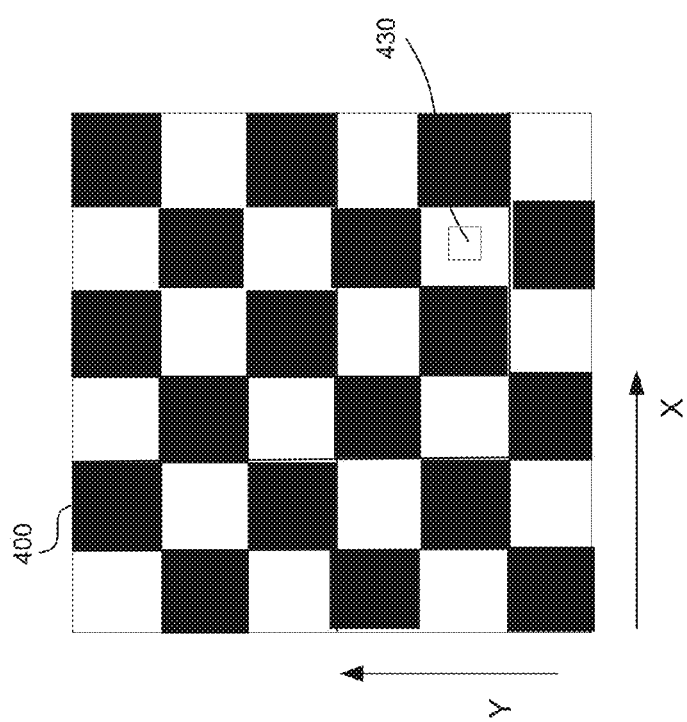
FIG. 4A shows a predetermined pattern displayed on the dual-mode region.

FIG. 4A shows a predetermined pattern displayed on the dual-mode region, while FIG. 4B shows the image of the predetermined pattern that is recorded by the light sensor 120 in FIG. 3. The predetermined pattern 400 can be a checkerboard as shown in FIG. 4A, a grid, a regular pattern, an irregular pattern, can be in color, etc. Preferably, the predetermined pattern 400 should not contain a 0 intensity pixel, i.e. a black pixel. In other words, each pixel in the pattern should emit a positive amount of light. Further, the predetermined pattern 400 should not contain a pixel whose intensity would saturate the light sensor 120. The light emitted by a pixel in the predetermined pattern 400 reflects off the residue 200 in FIG. 3 and reaches the light sensor 120. As a result the light sensor 120 records the image 410 in FIG. 4B, which contains brighter regions 420 due to the reflection of light off the residue 200. Each pixel 430 in the predetermined pattern 400 has a corresponding pixel 440 in the image 410. For example, the two pixels, 430, 440 can have an identical (X, Y) position. A processor can compare the pixel 430 in the predetermined pattern 400 to the corresponding pixel 440 in the image 410. If the two pixels differ by more than a predetermined threshold, the processor determines that the pixel 440 in the image 410 is influenced by the residue 200. The predetermined threshold can be 2% of the value of the pixel 430. By accumulating locations of all the pixels that are different between the predetermined pattern 400 and the image 410, the processor can determine the location of the residue 200 to be the image region 420.

Figure 5B:
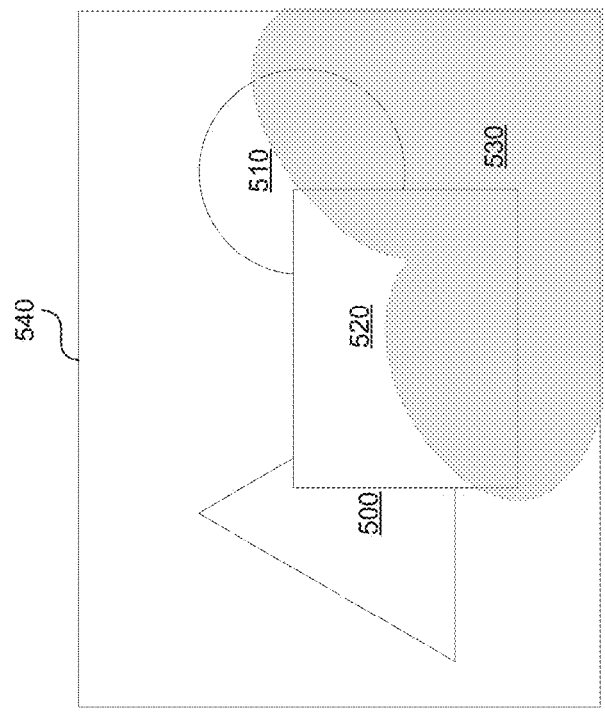
FIG. 5B shows an image of environment recorded by the light sensor through the residue, according to one embodiment.
Figure 5A:
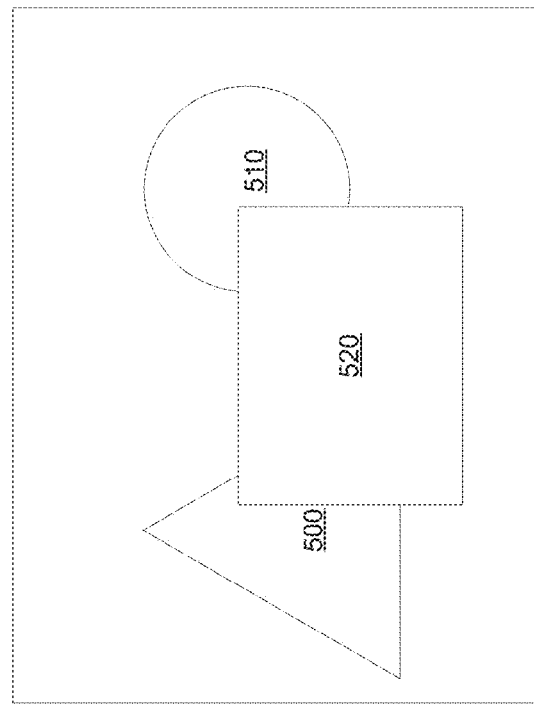
FIG. 5A shows environment surrounding the light sensor.

FIG. 5A shows environment surrounding the light sensor 120. FIG. 5B shows an image of environment recorded by the light sensor 120 through the residue 200, according to one embodiment. Environment contains shapes 500, 510, 520. A stained image 540 recorded by the light sensor 120 contains the region 530 covered with a residue, which results in pixels that are different from what the pixels should be if there is no residue. The pixels in the region 530 generally less bright than the pixels in the rest of the stained image 540. The processor associated with the light sensor 120 can perform several steps to correct the pixels in the region 530.

Figure 5C:
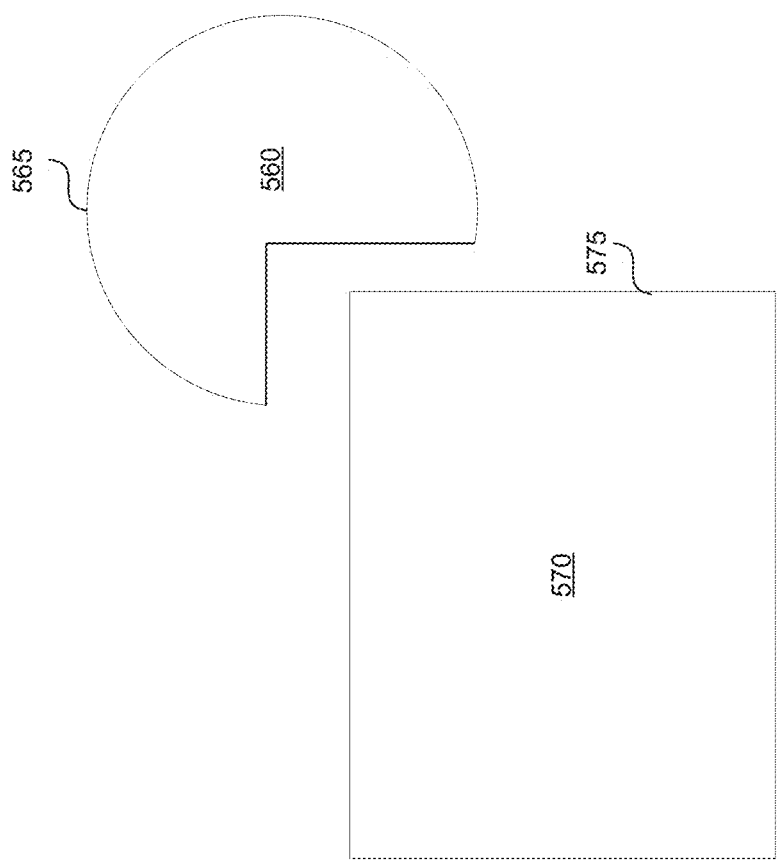
FIG. 5C shows objects identified by a processor in the stained image.
Figure 5C:
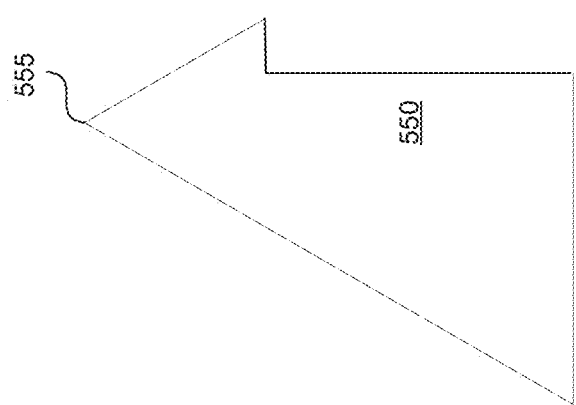

FIG. 5C shows objects identified by a processor in the stained image 540. The processor can identify the object depicted in the stained image 540 in FIG. 5B in several ways. In one embodiment, the processor can use a machine learning model, such as a neural network, to identify shapes and edges contained in the stained image 540 in FIG. 5B. In another embodiment, the processor can use an edge detection filter to identify the edges in the stained image 540, and subsequently the processor can connect the identified edges into shapes. As a result, the processor identifies shapes 550, 560, and 570, and their corresponding outlines 555, 565, 575. Identification of shapes 550, 560, 570 and their corresponding outlines 555, 565, 575 is important to avoid interpolation of pixel values across shape boundaries, as described in this application.

Figure 5D:
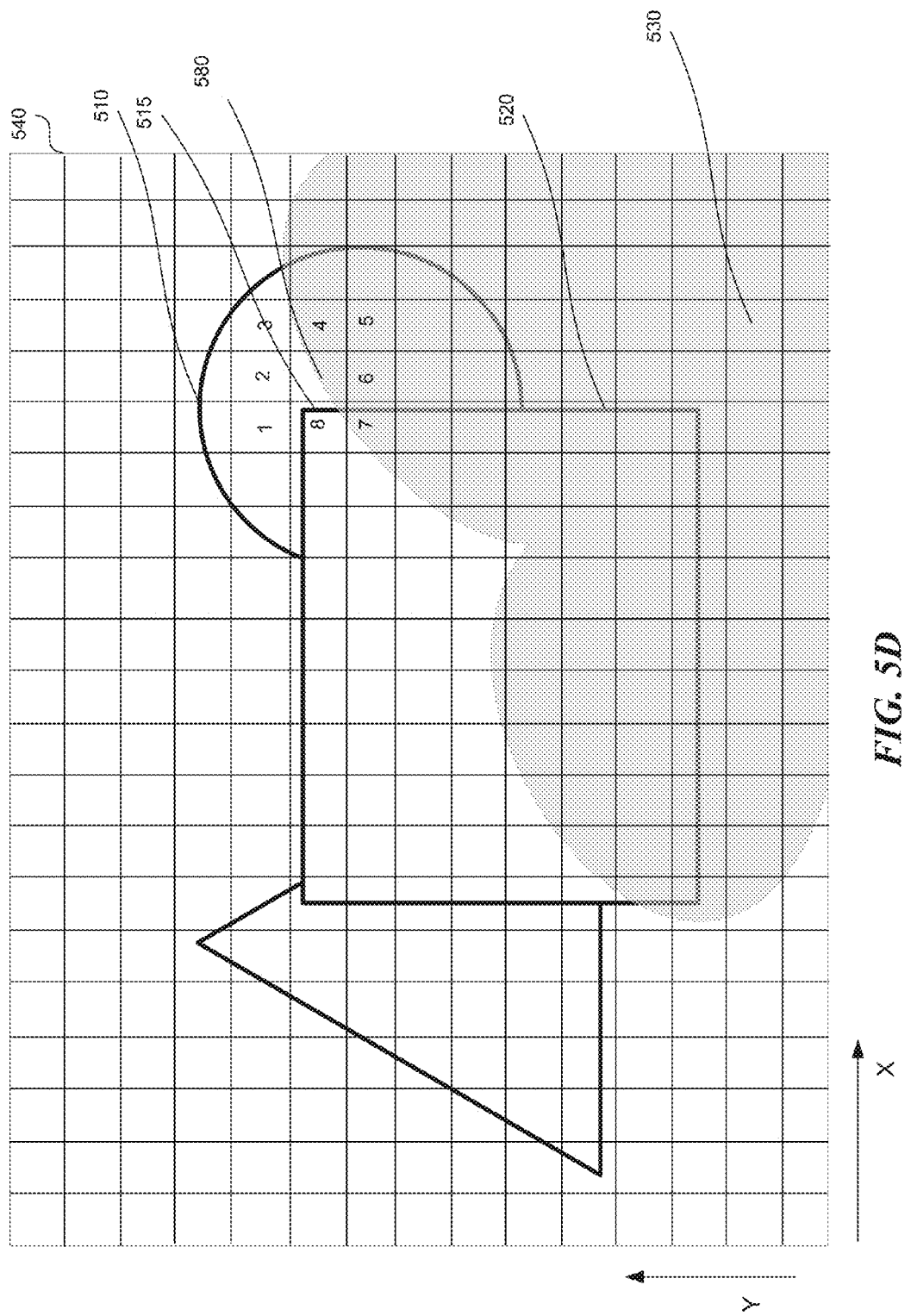
FIG. 5D shows calculation of a pixel in the resulting image
Figure 5E:
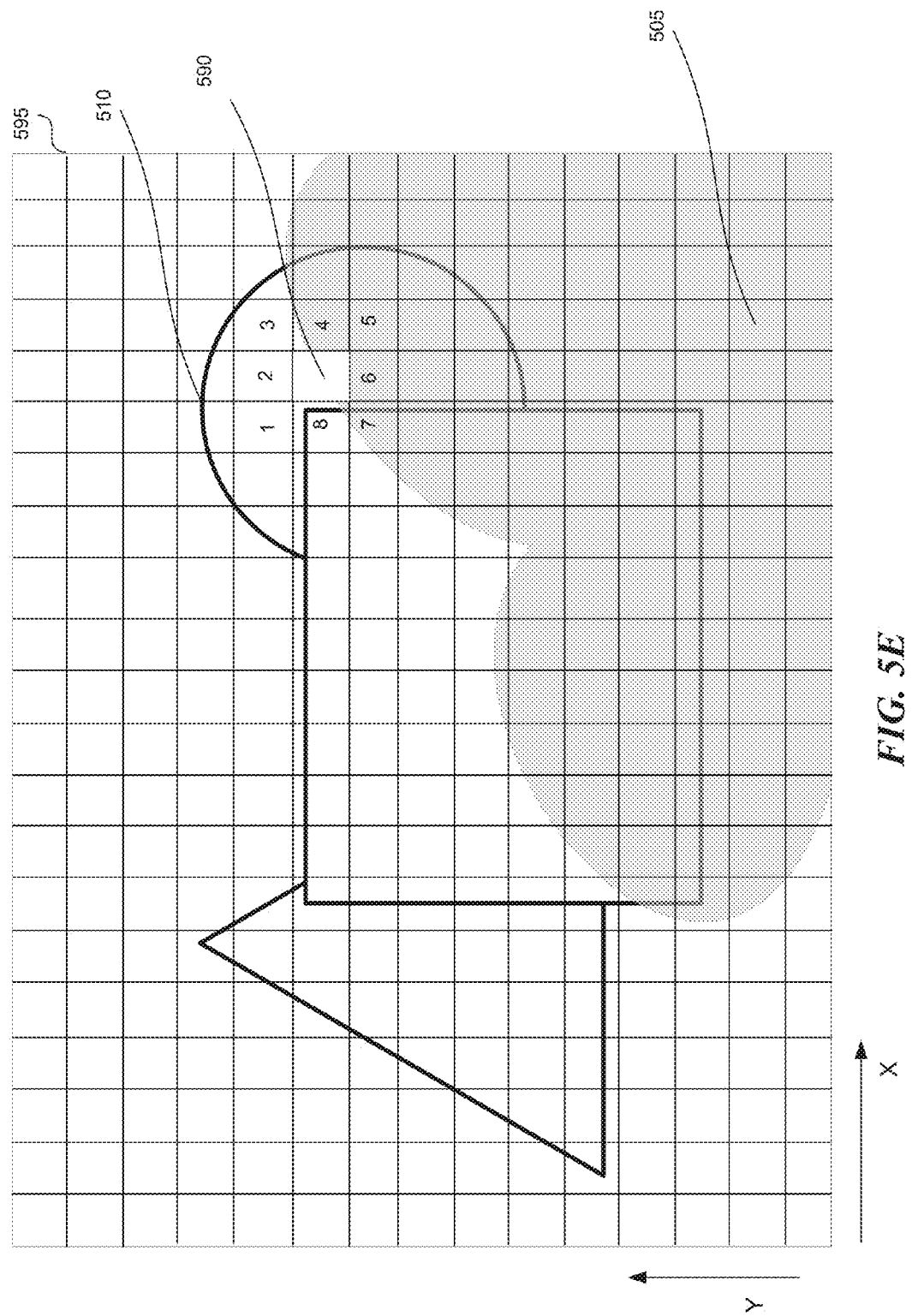
FIG. 5E shows the resulting pixel in the resulting image.

FIG. 5D shows calculation of a pixel in the resulting image FIG. 5E. Pixels in the image 540 that are outside of the residue region 530 do not need to be modified, and can be copied into the corresponding pixel from the resulting image. The corresponding pixel in the resulting image can have the identical (X, Y) position as the pixel in the image 540. For example, pixels 1, 2, 3, 8 in the image 540 can be copied into the resulting image. However, pixels contained in the residue region 530 have to be modified before being transferred into the resulting image. For example, pixels 580, 4, 5, 6, 7 need to be modified before being transferred into the resulting image.

For a given pixel 580, the processor computes a pixel neighborhood. The pixel neighborhood includes pixels close to the pixel 580. For example, the pixel neighborhood for them pixel 580 can include pixels 1-8. The pixel neighborhood of pixel 580 can also include 16 immediate neighbors surrounding pixels 1-8 (not labeled in the figure).

In one embodiment, to calculate the value of pixel 580 in the resulting image, the processor combines the values of pixels 1-3, and 8, because pixels 1-3, and 8 are outside of the residue region 530. To combine the values of the pixels 1-3, and 8, the processor can average the value of pixels 1-3 and 8. Alternatively, the processor can apply a different weight to each pixel 1-3, and 8, such that all the weights add up to 1.

In another embodiment, to calculate the value of pixel 580 and the resulting image, the processor combines the values of pixels 1-3, because pixel 8 and pixel 580 are separated by an edge 515 belonging to shape 520. Consequently, the value of pixel 8 should not contribute to the value of pixel 580 because pixel 8 may cause color bleeding from shape 520 to shape 510. To avoid including value of pixel 8 into the calculation of the resulting pixel 590 in FIG. 5E, the processor can determine the pixel neighborhood to contain pixels 1-6, because pixels 1-6 are not separated by an edge from pixel 580. Alternatively, to avoid including the value of pixel 8 into the calculation of the resulting pixel 590 in FIG. 5E, the processor can exclude from calculation all pixels separated by an edge from pixel 580. As described in this application, combining the values of pixels 1-3 can be done by averaging the value of pixels 1-3, or by applying different weights to each pixel 1-3, such that all weights add up to 1.

FIG. 5E shows the resulting pixel 590 in the resulting image. The resulting pixel 590 is computed by combining one or more pixels 1-8 in the pixel neighborhood surrounding pixel 580 in FIG. 5D. The resulting pixel 590 has the same (X, Y) position in the resulting image 595, as the (X, Y) position of pixel 580 in image 540. However, because the resulting pixel 590 is based on the pixels in the pixel neighborhood that are not included in the residue region 530 in FIG. 5D, pixel 590 is not contained in the residue region 505 in FIG. 5E.

Figure 6:
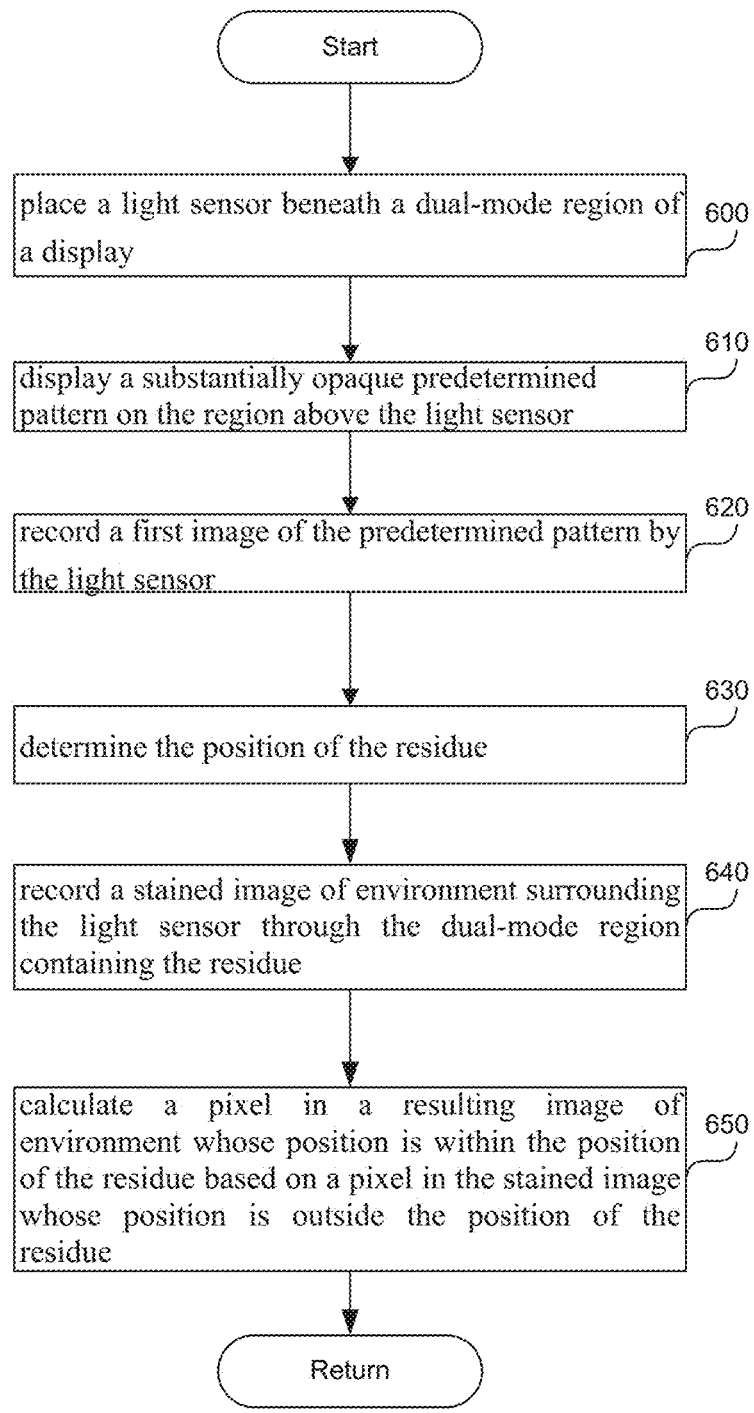
FIG. 6 is a flowchart of a method to produce a clean image by a sensor placed beneath a region with a residue, according to one embodiment.

FIG. 6 is a flowchart of a method to produce a clean image by a sensor placed beneath a region with a residue, according to one embodiment. In step 600, a light sensor is placed beneath a dual-mode region of a display. The dual-mode region can operate in a transparent mode allowing environment light to reach the light sensor and an opaque mode blocking environment light from reaching the light sensor. The dual-mode region contains a residue, for example residue 200 in FIG. 2A, FIG. 3.

In step 610, a display screen containing the dual-mode region displays a substantially opaque predetermined pattern on the region above the light sensor. The display screen can be an LCD display, can be an OLED display, AMOLED display, etc., as described in this application. The predetermined pattern can be a checkerboard as shown in FIG. 4A, a grid, a pattern of regular shapes, a pattern of irregular shapes, a colored pattern, etc., as long as the predetermined pattern is known to a processor controlling the display. The predetermined pattern should be substantially opaque, however not fully opaque, to allow light reflecting off the residue region to reach the light sensor. In step 620, the light sensor records a first image of the predetermined pattern. The operation of the display screen, the dual-mode region, the light sensor can be controlled by a processor.

In step 630, the processor determines the position of the residue by detecting a pixel in the first image that is different from a corresponding pixel in the predetermined pattern. The processor includes a position of the pixel in the first image into the position of the residue. In step 640, the light sensor records a stained image of environment surrounding the light sensor through the dual-mode region containing the residue.

In step 650, the processor calculates the resulting pixel 590 in FIG. 5E whose position is within the position of the residue, based on a pixel in the stained image whose position is outside the position of the residue. To calculate the pixel in the resulting image, the processor determines a pixel neighborhood associated with a pixel in the stained image, for example stained image 540 in FIG. 5D. The pixel neighborhood includes pixels surrounding the pixel under consideration. As described in FIG. 5B, the pixel neighborhood of pixel 580 can include pixels 1-8; pixels 1-3 and 8; pixels 1-3; or additional pixels surrounding pixels 1-8. Given the pixel 580 in FIG. 5D in the stained image 540 in FIG. 5D whose position is within the position of the residue 530 in FIG. 5D, the processor calculates the pixel 590 in FIG. 5E in the resulting image by combining each pixel in the pixel neighborhood whose position is outside of the position of the residue. The calculation can be performed iteratively for every pixel in the residue 530 in FIG. 5D. In one embodiment, the first pixels in the resulting image to be computed are the pixels within the position of the residue 530 in FIG. 5D, whose pixel neighborhood contains pixels outside of the updated residue 505 in FIG. 5E. If a pixel neighborhood does not contain any pixels outside of the updated residue 505 in FIG. 5E, the calculation of that resulting pixel is skipped, until the pixel neighborhood does contain pixels outside the updated residue 505 in FIG. 5E. Once all the resulting pixels have been computed, the processor can run a blur filter within boundaries of a shape, such as shape 510 in FIG. 5E.

To combine each pixel in the pixel neighborhood, the processor can average a pixel in the pixel neighborhood. Further, the processor can apply a weight to the pixel in the pixel neighborhood, such that all the weights applied add up to 1.

To determine the pixel neighborhood, the processor can identify an outline associated with one or more objects in the stained image, as described in the this application, for example outlines 555, 565, and 575 FIG. 5C. The processor can then determine the pixel neighborhood for the pixel 580 in FIG. 5D in the stained image 540 in FIG. 5D, such that the pixel neighborhood does not contain the outline associated with one or more objects in the stained image. For example, the pixel neighborhood can include pixels 1-3 in FIG. 5D.

Figure 7A:
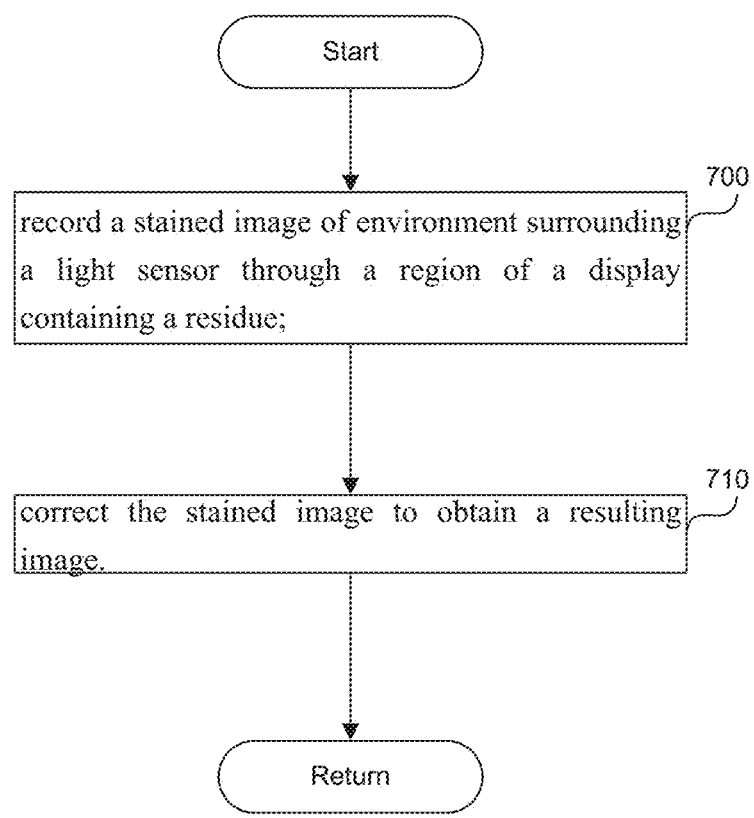
FIG. 7A is a flowchart of a method to produce a clean image by a sensor placed beneath a region with a residue, according to another embodiment.

FIG. 7A is a flowchart of a method to produce a clean image by a sensor placed beneath a region with a residue, according to another embodiment. FIG. 7B shows an image of environment recorded by the light sensor through the residue, according to another embodiment. In step 700, a light sensor records a stained image of environment surrounding the light sensor through a region of a display containing a residue.

In step 710, a processor associated with the light sensor corrects the stained image 780 in FIG. 7B to obtain a resulting image by identifying an outline 725, 735, 745 in FIG. 7B associated with one or more objects, such as 720, 730, 740 in FIG. 7B, in the stained image 780 in FIG. 7B, and smoothing a color within the outline associated with the one or more objects to obtain the resulting image. To correct the stained image, the processor can iteratively identify a second outline 750, 760, a third outline 770, etc., within the one or more objects, 720, 730, 740 in FIG. 7B, until no outline within an object can be further identified. Once all the outlines have been identified, the processor can smooth a color within the outlines 725, 735, 745, 750, 760, 770 in FIG. 7B to obtain the resulting image.

To identify the outlines 725, 735, 745, 750, 760, 770 in FIG. 7B, the processor can employ several methods. For example, the processor can detect a difference between neighboring pixels above a predetermined threshold to obtain a plurality of edge pixels, and connect the plurality of edge pixels into the outline associated with the one or more objects in the stained image. In another example, the processor can use machine learning model, such as a neural network, to identify outlines 725, 735, 745, 750, 760, 770 in FIG. 7B.

In one embodiment, to smooth the color within the outline in step 710, such as outlines 725, 735, 745, 750, 760, 770 in FIG. 7B, or outlines 555, 565, 575 in FIG. 5C, the processor can iteratively perform a blur filter within the outlines 725, 735, 745, 750, 760, 770 in FIG. 7B a predetermined number of times, such as 5 times.

In another embodiment, to smooth the color within the outline in step 710, the processor can display a substantially opaque predetermined pattern 300 in FIG. 3 on the region 125 in FIG. 3 above the light sensor 120 in FIG. 3. The predetermined pattern 300 in FIG. 3 can be a checkerboard pattern, a grid, a pattern of irregular shapes, a pattern of irregular shapes, can be colored, etc. The pattern can be substantially opaque, even reaching full opacity. The exposure of the light sensor 120 can be long enough to allow light reflecting off the residue region 200 and FIG. 3 to reach the light sensor 120. The display can be an LCD display, an OLED display, an AMOLED display, etc. The processor records a first image of the predetermined pattern by the light sensor.

To smooth the color within the outline in step 710, the processor determines the position of the residue by detecting a position of a pixel in the first image that is different from a corresponding pixel in the predetermined pattern, such as pixel 580 in FIG. 5D. Once such a pixel is detected by the processor, the processor adds the position of the pixel to the position of the residue. Finally, based on a pixel in the stained image, such as pixels 1-3, and 8 in FIG. 5B, whose position is outside the position of the residue 530 in FIG. 5D, the processor calculates a pixel in the resulting image, such as pixel 590 in FIG. 5E. Once the resulting pixel 590 has been calculated, the position of the residue 530 in FIG. 5D is reduced to take out the position of the pixel 590 in FIG. 5E. The new residue becomes the updated residue 505 in FIG. 5E. As can be seen in FIG. 5E, upon calculating the resulting pixel 590 the position of the pixel 590 in the resulting image 595 is outside of the position of the updated residue 505. As new pixels are computed in the resulting image, the position of the residue 505 is updated continuously to take out the positions of the pixels that have been computed.

To calculate the pixel in the resulting image, the processor determines a pixel neighborhood, such as pixels 1-8 in FIG. 5D, associated with a pixel, such as pixel 580 in FIG. 5D, in the stained image, such as image 540 in FIG. 5D. Given the pixel, such as pixel 580 in FIG. 5B, in the stained image, 540 in FIG. 5E, whose position is within the position of the residue 530 in FIG. 5D, calculating the pixel 590 in FIG. 5E in the resulting image 595 in FIG. 5E, by combining each pixel, 1-3, and 8 in FIG. 5D, in the pixel neighborhood whose position is outside of the position of the residue. The calculation can be performed iteratively for every pixel in the residue 530 in FIG. 5D. In one embodiment, the first pixels in the resulting image to be computed are the pixels within the position of the residue 530 in FIG. 5D, whose pixel neighborhood contains pixels outside of the residue 530 in FIG. 5D. If a pixel neighborhood does not contain any pixels outside of the updated residue 505 in FIG. 5E, the calculation of that resulting pixel is skipped, until the pixel neighborhood does contain pixels outside the updated residue 505 in FIG. 5E. Once all the resulting pixels have been computed, the processor can run a blur filter within boundaries of a shape, such as shape 510 in FIG. 5D.

To determine the pixel neighborhood, the processor checks whether a potential pixel for inclusion into the pixel neighborhood, such as pixels 1-8 in FIG. 5D is not separated by an outline, such as an outline 555, 565, 575 in FIG. 5C from the pixel under consideration, such as pixel 580 in FIG. 5D.

Computer

Figure 8:
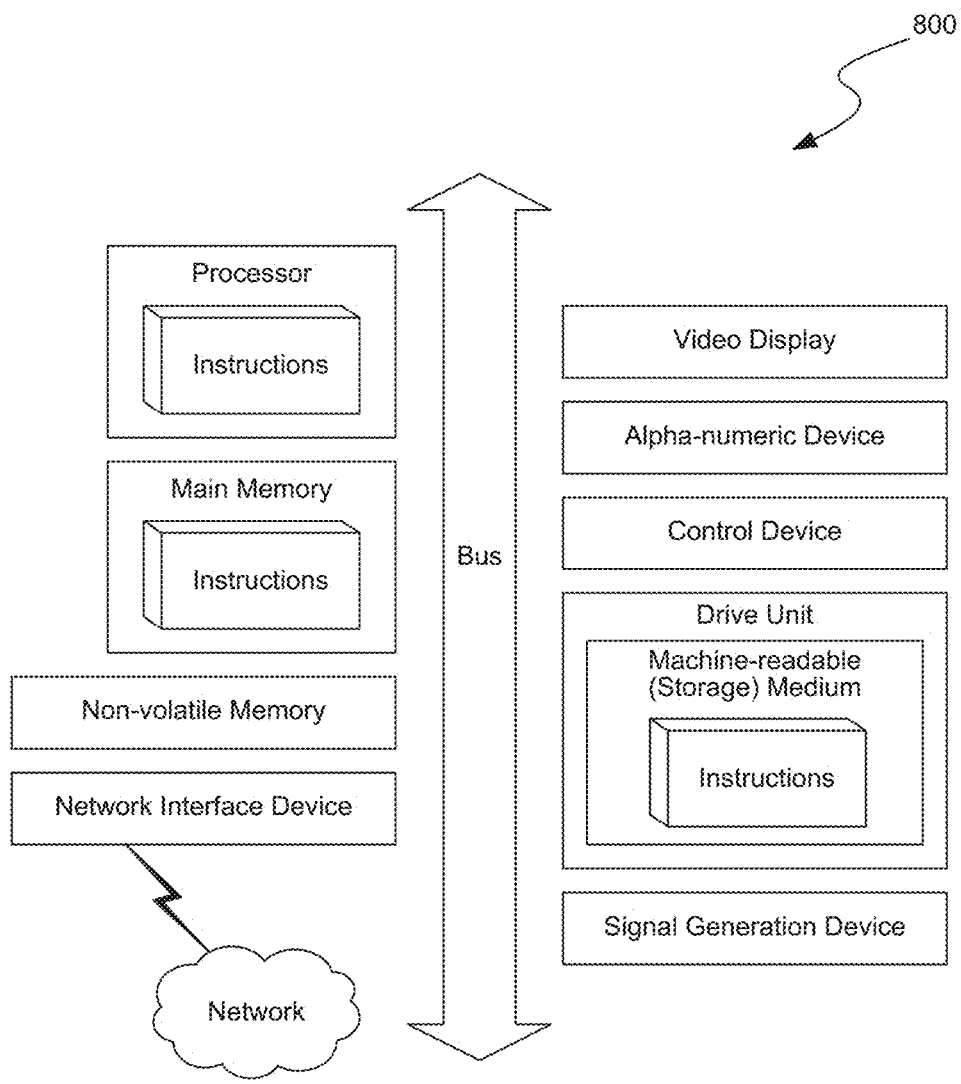
FIG. 8 is a diagrammatic representation of a machine in the example form of a computer system 800 within which a set of instructions, for causing the machine to perform any one or more of the methodologies or modules discussed herein, may be executed.

FIG. 8 is a diagrammatic representation of a machine in the example form of a computer system 800 within which a set of instructions, for causing the machine to perform any one or more of the methodologies or modules discussed herein, may be executed.

In the example of FIG. 8, the computer system 800 includes a processor, memory, non-volatile memory, and an interface device. Various common components (e.g., cache memory) are omitted for illustrative simplicity. The computer system 800 is intended to illustrate a hardware device on which any of the components described in the example of FIGS. 1-7B (and any other components described in this specification) can be implemented. The computer system 800 can be of any applicable known or convenient type. The components of the computer system 800 can be coupled together via a bus or through some other known or convenient device.

The processor in FIG. 8 can be the processor performing various image processing techniques described in this application. The processor in FIG. 8 can be associated with a mobile device 100 in FIGS. 1A, 1B, 2B, 3, etc. Display in FIG. 8 can be a display 110 in FIGS. 1A, 1B, 2A, 2B, 3 etc. The display in FIG. 8 can include the region 125 in FIGS. 1A, 1B, 2A, 2B, 3 containing the residue described in this application.

This disclosure contemplates the computer system 800 taking any suitable physical form. As example and not by way of limitation, computer system 800 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, computer system 800 may include one or more computer systems 800; be unitary or distributed; span multiple locations; span multiple machines; or reside in a cloud, which may include one or more cloud components in one or more networks. Where appropriate, one or more computer systems 800 may perform without substantial spatial or temporal limitation one or more steps of one or more methods described or illustrated herein. As an example and not by way of limitation, one or more computer systems 800 may perform in real time or in batch mode one or more steps of one or more methods described or illustrated herein. One or more computer systems 800 may perform at different times or at different locations one or more steps of one or more methods described or illustrated herein, where appropriate.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 800. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, storing and entire large program in memory may not even be possible. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system 800. The interface can include an analog modem, isdn modem, cable modem, token ring interface, satellite transmission interface (e.g. "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of FIG. 8 reside in the interface.

In operation, the computer system 800 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux™ operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may thus be implemented using a variety of programming languages.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies or modules of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and storage of charge or a release of stored charge. Likewise, in other memory devices, a change of state may comprise a physical change or transformation in magnetic orientation or a physical change or transformation in molecular structure, such as from crystalline to amorphous or vice versa. The foregoing is not intended to be an exhaustive list in which a change in state for a binary one to a binary zero or vice-versa in a memory device may comprise a transformation, such as a physical transformation. Rather, the foregoing is intended as illustrative examples.

A storage medium typically may be non-transitory or comprise a non-transitory device. In this context, a non-transitory storage medium may include a device that is tangible, meaning that the device has a concrete physical form, although the device may change its physical state. Thus, for example, non-transitory refers to a device remaining tangible despite this change in state.

REMARKS

The language used in the specification has been principally selected for readability and instructional purposes, and it may not have been selected to delineate or circumscribe the inventive subject matter. It is therefore intended that the scope of the invention be limited not by this Detailed Description, but rather by any claims that issue on an application based hereon. Accordingly, the disclosure of various embodiments is intended to be illustrative, but not limiting, of the scope of the embodiments, which is set forth in the following claims.

The invention claimed is:

1. A method comprising:
 placing a light sensor beneath a dual-mode region of a display, the dual-mode region comprising a transparent mode allowing environment light to reach the light sensor and an opaque mode blocking environment light from reaching the light sensor, wherein the dual-mode region contains a residue;
 displaying a predetermined pattern on the dual-mode region above the light sensor;
 recording a first image of the predetermined pattern by the light sensor;

determining a position of the residue by detecting a pixel in the first image that is different from a corresponding pixel in the predetermined pattern, and including a position of the pixel in the first image into the position of the residue;

recording a stained image of environment surrounding the light sensor through the dual-mode region containing the residue; and calculating a pixel in a resulting image of environment whose position is within the position of the residue based on a pixel in the stained image whose position is outside the position of the residue.

2. The method of claim 1, said calculating the pixel in the resulting image comprising:

determining a pixel neighborhood associated with the pixel in the stained image;

given the pixel in the stained image whose position is within the position of the residue, calculating the pixel in the resulting image by combining each pixel in the pixel neighborhood whose position is outside of the position of the residue.

3. The method of claim 2, said combining each pixel in the pixel neighborhood comprising averaging each pixel in the pixel neighborhood.

4. The method of claim 2, said determining the pixel neighborhood comprising:

identifying an outline associated with one or more objects in the stained image; and determining the pixel neighborhood for the pixel in the stained image, wherein the pixel neighborhood does not contain the outline associated with the one or more objects in the stained image.

5. A system comprising:

a dual-mode region of a display containing a residue, the dual-mode region comprising a transparent mode and an opaque mode;

a light sensor disposed beneath the dual-mode region of the display, the transparent mode allowing environment light to reach the light sensor, and the opaque mode blocking environment light from reaching the light sensor;

a processor creating a resulting image of environment surrounding the light sensor, the processor:

sending a first control signal to the dual-mode region to display a predetermined pattern on the dual-mode region above the light sensor;

sending a second control signal to the light sensor to record a first image of the predetermined pattern;

sending a third control signal to the dual-mode region to become transparent;

sending a fourth control signal to the light sensor to record a stained image of environment surrounding the light sensor through the transparent dual-mode region;

recording the stained image of environment surrounding the light sensor through the dual-mode region containing the residue; and calculating a pixel in the resulting image of environment based on a pixel in the stained image whose position is outside a position of the residue, wherein a position of the pixel in the resulting image is within the position of the residue.

6. The system of claim 5, the predetermined pattern comprising a checkerboard pattern.

7. The system of claim 5, the light sensor comprising at least one of a camera, an ambient light sensor, or a proximity sensor.

8. The system of claim 5, comprising oleophobic coating applied to the dual-mode region.

9. The system of claim 5, said processor calculating the pixel in the resulting image comprising:

said processor determining a pixel neighborhood associated with the pixel in the stained image; and given the pixel in the stained image whose position is within the position of the residue, said processor calculating the pixel in the resulting image by combining each pixel in the pixel neighborhood whose position is outside of the position of the residue.

10. The system of claim 9, said processor combining each pixel in the pixel neighborhood comprising:

said processor averaging each pixel in the pixel neighborhood whose position is outside of the position of the residue.

11. The system of claim 9, said processor determining the pixel neighborhood comprising:

said processor identifying an outline associated with one or more objects in the stained image; and said processor determining the pixel neighborhood for the pixel in the stained image, wherein the pixel neighborhood does not contain the outline associated with the one or more objects in the stained image.

* * * * *